United States Patent [19]

Stern

[11] Patent Number: 5,627,323

[45] Date of Patent: May 6, 1997

[54] ULTRASONIC BINARY GAS MEASURING DEVICE

[76] Inventor: Michael Stern, 2505 Oakrill Rd., Marietta, Ga. 30062

[21] Appl. No.: 450,580

[22] Filed: May 25, 1995

[51] Int. Cl.⁶ .................................................. G01F 1/00
[52] U.S. Cl. ......................... 73/861.28; 73/24.06
[58] Field of Search ..................... 73/861.27, 861.28, 73/861.29, 24.01, 25.01, 24.06, 24.05

[56] References Cited

U.S. PATENT DOCUMENTS

| | | | |
|---|---|---|---|
| 5,060,506 | 10/1991 | Douglas | 73/24.01 |
| 5,060,514 | 10/1991 | Aylsworth | 73/24.06 |
| 5,247,826 | 10/1993 | Frola et al. | 73/24.01 |
| 5,392,635 | 2/1995 | Cadet et al. | 73/24.01 |

*Primary Examiner*—George M. Dombroske
*Assistant Examiner*—Ronald Biegel

[57] ABSTRACT

A method and apparatus to continuously measure the ratio of gasses in a binary gas mixture. A binary gas mixture is passed through a chamber in which a single ultrasonic wave travels from one piezoelectric transducer to another on the opposite side of the chamber. Immediately upon sensing an incoming ultrasonic wave, the transducer on opposite side of the chamber converts into a transmitter and transmits a single wave on top of the just received wave. The new wave travels back in the direction of the first transducer where it is received. The time of travel back and forth through the chamber is compared to a reference time, and represents the concentration of a gas in a binary gas mixture. The difference between time of travel in the direction of flow and against the direction of flow represents standard flow rate. A temperature sensor located in the middle of the chamber is used to temperature compensate the result. From the measured times, the temperature, the offset, and stored formulas a microprocessor calculates the gas concentration and/or the standard flow rate for the gas.

25 Claims, 7 Drawing Sheets

ULTRASONIC BINARY GAS MEASURING DEVICE

TECHNICAL FIELD

The invention relates to sensors and more particularly to gas concentration sensors, suitable, for example, for indicating the concentration and flow rate of oxygen in gas delivered to a patient for medical purposes.

BACKGROUND ART

Various types of sensors have been designed for measuring properties of gas. Some of these sensors were designed to measure a specific component of a gas in a given gas mixture. For example oxygen concentrators may be used to remove the carbon dioxide and nitrogen from air. This leaves a pre-defined mixture of oxygen and argon which is not removed by the concentrator. It is desired to indicate to the patient the purity of oxygen concentration delivered by his concentrator. It is also desirable to indicate the delivered gas flow rate which may be critical to remain constant. Sensors may be used to verify that the prescribed gas delivery requirements are met.

Douglas U.S. Pat. No. 5,060,506 describes a cylindrical chamber with piezoelectric transducers mounted on diametrically opposite sides of the chamber and are aligned along an axis inclined to the axis of gas flow through the chamber for measuring the concentration of a gas constituent. Transmitting transducer is excited by short pulse trains. Between excitations there is a waiting period needed to dispose of standing waves. However, in the Douglas apparatus a very short chamber (1.5 inches, 3.81 cm) allows only very small gas sample which increases accuracy dependence no extraneous factors such as mechanical degradation and long term drift. Low flow velocity inside the sensing chamber provides no meaningfully different travel times in and against the direction of flow. Together, these introduce low signal to noise ratio and high drift of the sensor calibration point effected by variations in mechanical properties of the chamber as a result of temperature and time.

Frola et al U.S. Pat. No. 5,247,826 describes a narrow coiled tube with two piezoelectric transducers mounted on its opposite sides and aligned along the axis of the tube. Temperature sensing thermistor wire is placed in the center of the tube. Piezoelectric transducers are energized periodically and bursts of ultrasonic energy are emitted into the tube in the direction of the receiver. The gas concentration reading is effected by the temperature of the gas, the flow rate, the path length between the sensors, and by the gas composition. The time required for the resulting ultrasonic wave to reach the other side of the tube is measured. To cancel the effect of flow on travel time, the two piezoelectric transducers alternately operate as transmitter and receiver. Travel time in the direction of flow and against the direction of flow is recorded. The two ultrasonic wave travel times and the temperature of the gas are used to calculate the standard gas flow rate and concentration of oxygen in the gas. However, this apparatus utilizes a long and flexible tube, which significantly increases the sensor size (6×4.5×1.5 inches, 15.2×10.1×3.8 cm). Tube is made of soft plastic material which can cause further complications as a result of dimensional changes in the flexible-coiled tube length as a result of temperature and time.

Aylsworth U.S. Pat. No. 5,060,514 describes a cylindrical chamber with piezoelectric transducers mounted on diametrically opposite sides of the chamber and are aliened along an axis inclined to the axis of gas flow through the chamber for measuring the concentration of a gas constituent. Transmitting transducer is energized by an endless pulse train, and phase difference between transmitted pulses and received pulses is detected at the receiver. However, this approach relies heavily on laminar flow inside the cylindrical chamber which is very difficult to achieve. Moreover, endless pulse train approach generates standing waves which introduce system inaccuracies and complicate system calibration.

Other commercially available sensors utilize galvanic or ceramic fuel sells to measure oxygen and other gas concentrations. However, these sensors require frequent calibration, their life time is limited, their response time is long, and they utilize very high temperature which entails high power consumption by the sensor (2 w to 10 w).

SUMMARY OF THE INVENTION

The invention contemplates the measurement of gaseous components and standard flow with far greater accuracy. It incorporates unique methods, and apparatus constructed of components provided therein. It provides a gas analyzer such as needed in an oxygen concentrator where an economical and accurate oxygen concentration in an oxygen/nitrogen mixture can be measured. Response to change in concentration is virtually immediate. Sensor is compact, energy efficient, routine replacement of parts is unnecessary, calibration is very simple, and accuracy is better than 2%.

The present invention utilizes the physical phenomena of different sound traveling speeds through different media. It also utilizes the fact that piezoelectric transducers resonate at their own resonant frequency for a while after receiving a single wave. For binary gasses, as concentration of one gas constituent decreases, the concentration of another increases, thus the speed of sound through the gas mixture approaches the nominal speed of sound of the more concentrated gas. Longer ultrasonic wave travel path through the gas sample yields better resolution of gas concentration and flow rate, however it also increases the attenuation and thus decreases the amplitude of the ultrasonic wave at the receiver. The sensor includes two ultrasonic transducers which are mounted on opposite sides of an 11 cm long cylindrical chamber and are aligned along an axis inclined to the direction of flow inside the chamber. The gas enters through an opening in the side of the chamber and flows to the other side of the chamber where it exits the sensor through a similar opening in the chamber.

Periodically one of the transducer is energized with a single wave, composed of a single positive and single negative cycles, at the nominal transducer frequency. A resulting ultrasonic wave travels to the opposite side of the chamber where the second transducer is positioned. Utilizing fast microprocessor digital signal processing technology, the second transducer detects the incoming wave, changes its role to a transmitter, and superimposes a new wave on top of the wave which it just started to receive. As a result an amplified echo effect is achieved. The first transducer takes a role of a receiver and receives the echoed wave. Based on forth and back travel time, temperature, stored calibration values, and equations a microprocessor determines the concentration of oxygen or of other component of the gas. Difference between travel time in the direction of flow and travel time against the direction of flow determines the standard flow rate.

This design of the ultrasonic cell provides twice longer path of travel than if the travel path was only in one direction. The twice longer path through the tube increases the accuracy of the sensor, but still keeps the compact sensor structure. Large gas sample reduces the effect of manufacturing tolerances and long term drift, and calibration is simplified. The rigid structure of the flow tube reduces long term deterioration of sensor accuracy.

DESCRIPTION OF DRAWINGS

In the accompanying drawings which form a part of the specification and are to be read in conjunction with and in which like reference numbers are used to indicate like parts an the various views:

FIG. 3 provides a schematic of the cross-sectional view of the measuring device of this invention disclosing the passage of gas there through.

DETAILED DESCRIPTION OF THE INVENTION

Figure 1:
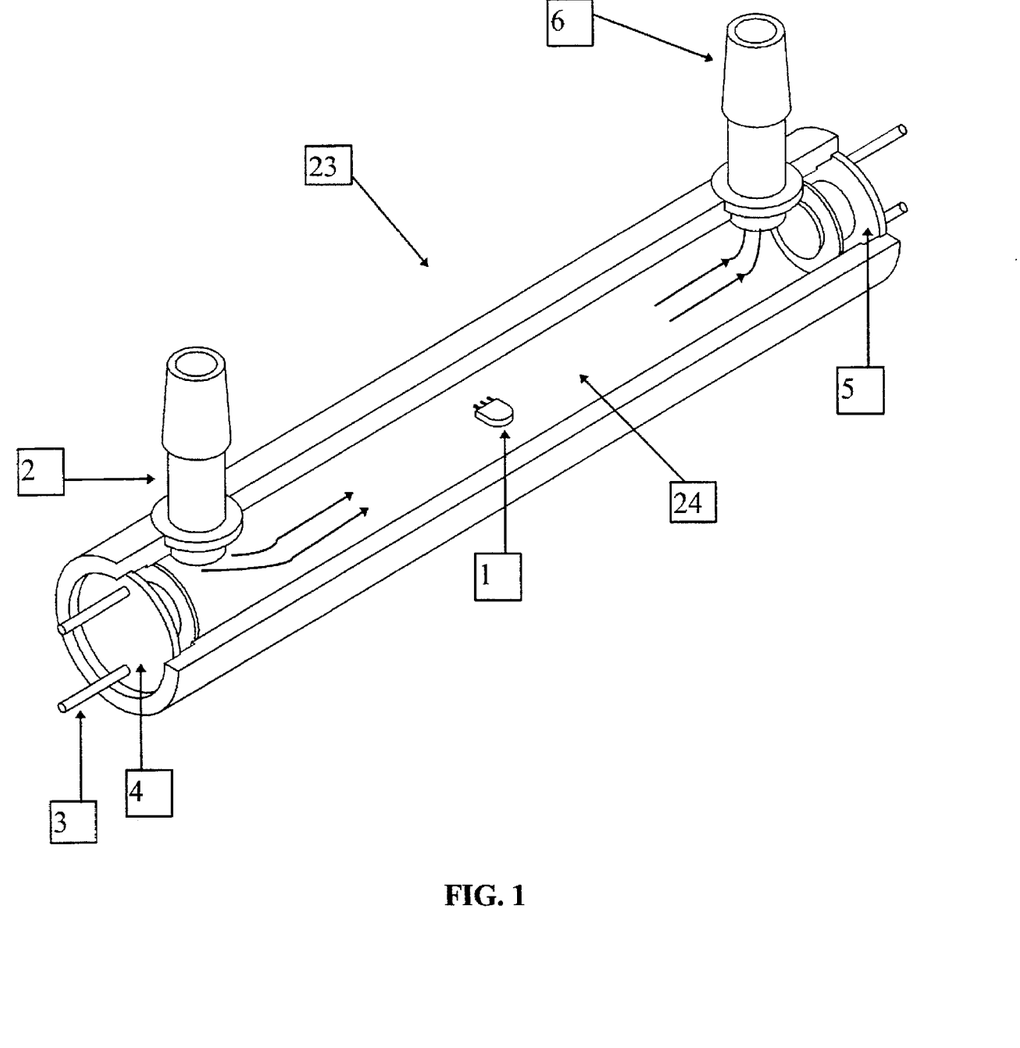
FIG. 1 provides an isometric view, partially cutaway, of the ultrasonic gas measuring device of this invention.

Referring to the drawings, and in particular FIG. 1, FIG. 5, FIG. 6, and FIG. 7 the ultrasound gas measuring device 23 of the invention is clearly disclosed. The ultrasonic cell 23 includes a housing of rather cylindrical shape. The cylinder incorporates an inner chamber 24, and inside this chamber the gas concentration and flow rate are detected. Two piezoelectric transducers 4 and 5 are attached to the outer sides of the chamber by means of non out-gassing epoxy glue. As glue molecules are usually very large and heavy, even small out-gassing of the glue will adversely effect the tolerance of the result. Gas entrance and exit from the chamber is accomplished by means of two barbs 2 and 6. The distance between the two piezoelectric transducers is 11 cm, which guarantees large enough gas sample 22 inside the chamber. FIG. 1 depicts gas flow lines inside the chamber, which is a possible direction of gas flow. However, opposite flow direction is also possible. Temperature sensor 1 is located in the middle of the chamber and its leads are sealed to the sensor housing by means of non out-gassing epoxy glue. This sensor needs to be as accurate and as fast as possible. Good accuracy of the temperature measurement will eliminate the need for individual temperature calibration, and fast response will decrease the lag between temperature compensation and system response to rapid temperature changes.

The immediate re-transmission of incoming wave by the receiver, generates path doubling effect. This produces effective chamber length of 22 cm and thus increases the effective gas sample, which improves the system tolerance and performance.

Entrance and exit of gas through chamber side generates close to uniform turbulent flow inside the chamber. Complex design considerations were necessary in the past to assure laminar flow at the transducers. Uniform turbulent flow approach, inner diameter of the chamber of less that two times the ultrasound wavelength but more than one wavelength, and flow path at least 10 wavelengths long, causes the flow rate inside the chamber to average out thus canceling the effect of turbulence no measurement. While actual path of the ultrasonic wave is 22 cm long, attenuation occurs only along an 11 cm path after which a new signal is re-transmitted in opposite direction, such that the attenuation path is only half of the total travel path of the ultrasonic wave. This reduces the effect of chamber attenuation which is proportional to square of the chamber length.

Figure 5:
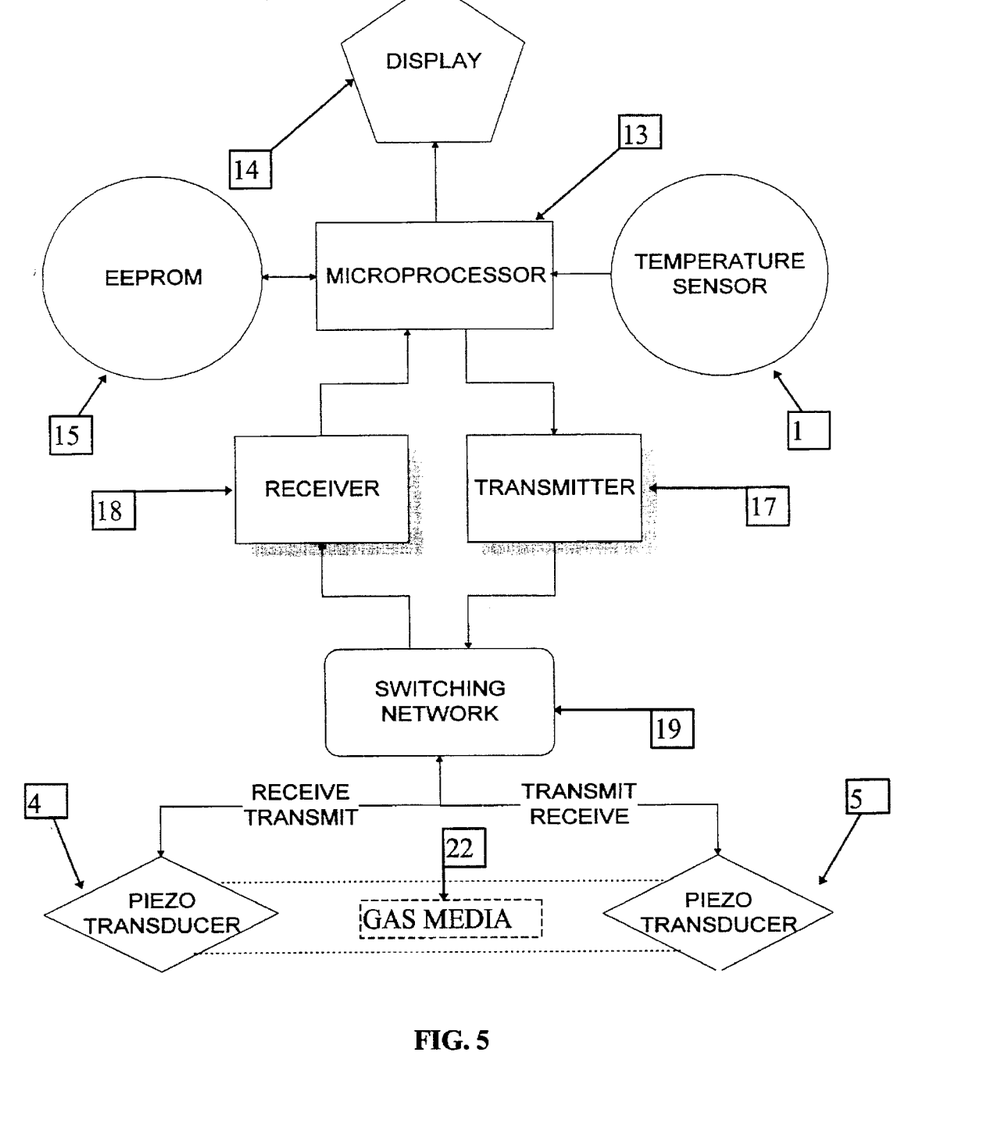
FIG. 5 provides a schematic block diagram showing circuitry for operating the sensor of this invention.

In operation the piezoelectric transducer 4 is energized by means of a single 10 v p—p wave. Although transducers 4 & 5 can be energized by a train of pulses, it is preferable to use a single wave to excite the transmitting transducer. Train of transmitted pulses will cause the receiver to receive new pulses at the time that it already resonates at its resonant frequency. This will cause some inaccuracies in measurements as a result of minor differences between the frequency of the transmitted wave and the resonant frequency of the receiver, which will add some unwanted harmonics and reduce the overall system accuracy. A single wave also reduces power consumption, and reduces amount of standing waves over the pulse train approach. The wave causes piezoelectric transducer 4 to generate an ultrasonic wave which travels through the chamber 24 to transducer 5. At the time of wave arrival at transducer 5 no calculation is performed, thus minimizing the effect of delay on the final tolerance of the resulting concentration. Instead, as soon as wave arrives at transducer 5, it is immediately re-transmitted back, towards transducer 4, by means of fast wave incident detection accomplished by a fast preferably Reduced Instruction Set of RISC microprocessor with internal frequency at least 125 times higher than the frequency of the ultrasound wave. As it takes a RISC microprocessor only 5 internal clock cycles to detect an incoming wave and re-transmit it, this time is insignificant in comparison to ultrasonic wave length. For example, if microprocessor internal clock is 10 MHz and transmitted wave is at 40 KHz, wave in opposite direction can be generated within a delay of 2% of the wave length of the incident ultrasonic wave. As this detection delay is always constant, it is offset by the offset value stored in the EEPROM 15. When wave arrives back at transducer 4, microprocessor waits a predetermined time, which is the time it takes the transducer to resonate to its peak amplitude. Then the time from initial transmission to the time of peak amplitude at receiver 26 is sampled and converted to gas constituent concentration.

The speed at which the ultrasonic wave travels through the chamber is effected by gas concentration, gas flow rate, and temperature. To compensate for temperature effects, temperature sensor 1 feeds temperature data to microprocessor 13. Flow rate effect is canceled out by the fact that the ultrasonic wave travels back and forth through the chamber 24. Thus flow rate effect in forward direction will cancel out the flow rate effect in reverse direction.

Flow rate measurement is accomplished via determining the absolute value of difference between time of travel in the direction of flow and time of travel against the direction of flow. This measurement is independent of temperature and pressure effects, and is only effected by flow rate and changes in the physical properties of chamber 24.

Figure 2:
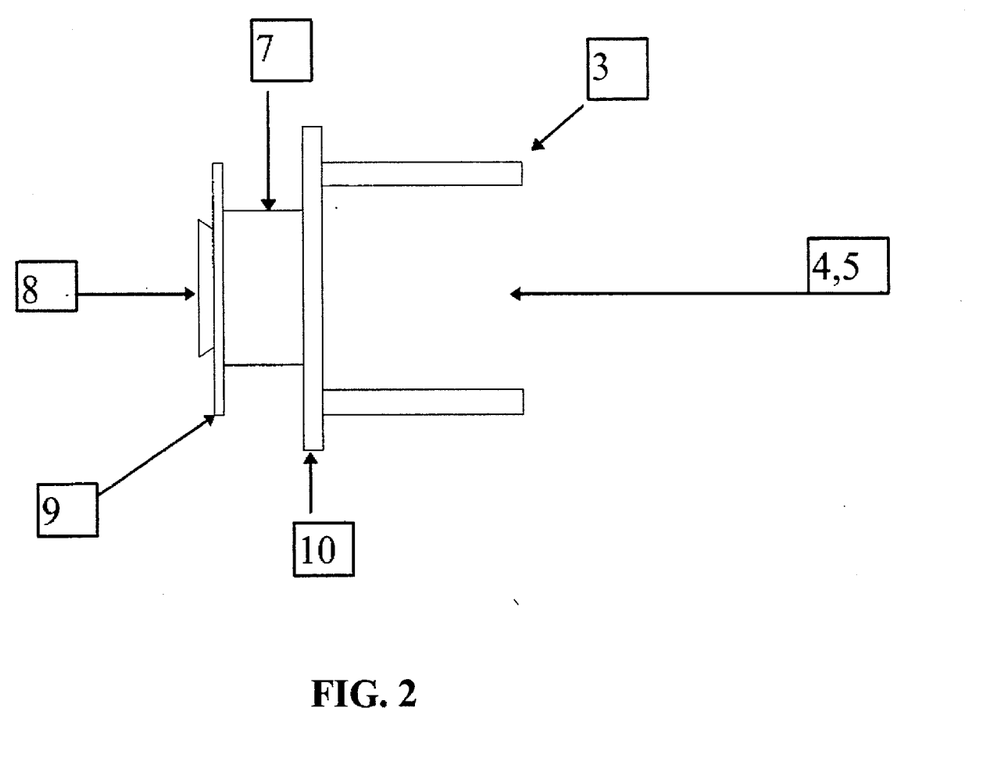
FIG. 2 provides a cross sectional view through the piezoelectric transducer of the gas monitoring device.

In reference to FIG. 2, the piezoelectric transducer for this development is accurately shown. It can be seen that the transducer includes a horn 8, which narrows the ultrasonic wave beam. Piezoelectric element 9 is mounted on a substrate 7. Contacts 3 connect to negative and positive poles of the piezoelectric element 9.

Figure 3:
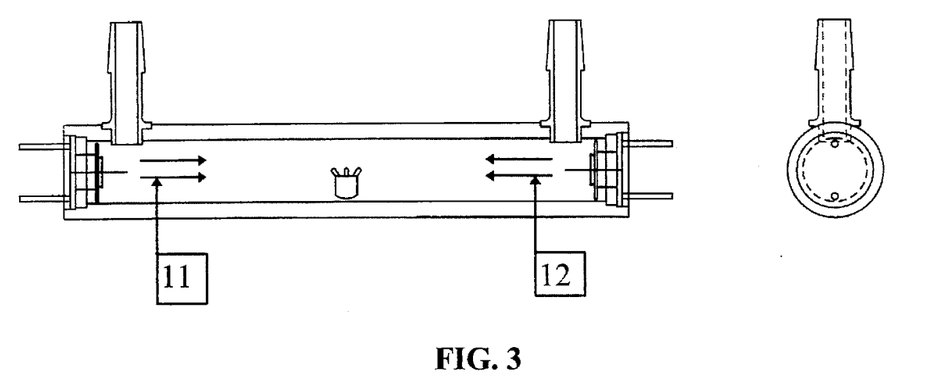

In referring to FIG. 3 the actual direction of transmission is more accurately disclosed. As can be seen, the ultrasonic wave 11 travels from the transmitter to a receiver first, then immediately upon arrival, the receiver transmitter pair change roles and the wave 12 travels back to the receiver which just changed its role from a transmitter.

Figure 4:
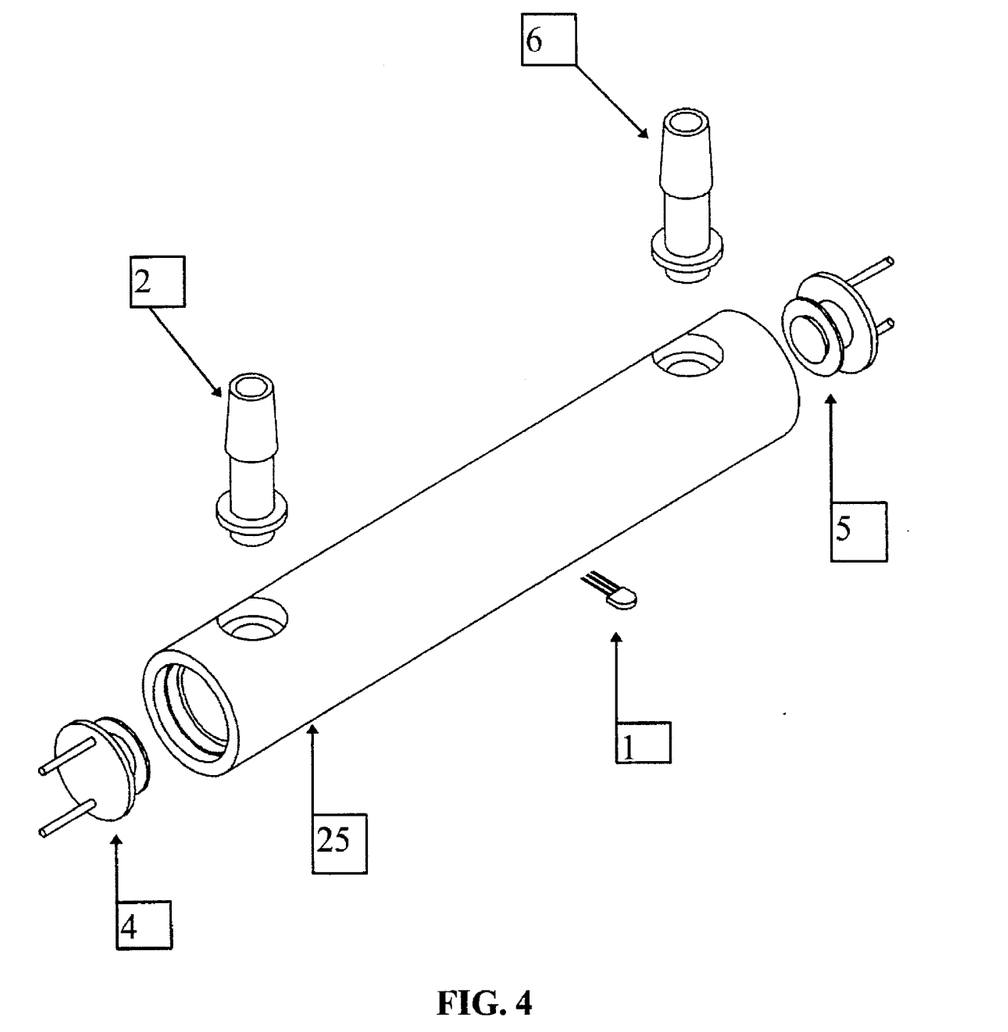
FIG. 4 provides an exploded view, in perspective, of the gas monitoring device.

In referring to FIG. 4 the actual assembly drawing of the ultrasonic device is more accurately disclosed. All parts assembled on the cylindrical housing 25 are sealed by means of non out-gassing epoxy glue.

In reference to FIG. 5 the actual block diagram of the device electronic circuit is accurately disclosed. Microprocessor 13 receives temperature information from temperature sensor 1, offset information from Electrically Erasable and Programmable Memory or EEPROM 15, and time information from receiver 18. It energizes the transmitter piezoelectric transducer via transmitter 17. Received information is compiled into gas constituent concentration and standard gas flow rate. Piezoelectric transducers exchange their role from transmitter to receiver by means of a switching network 19. During calibration microprocessor 13 expects a known gas concentration at zero flow rate. It computes and stores in EEPROM 15 gas concentration offset and zero flow offset, which are inherent from variations in mechanical structure between different transducer elements 23. During normal operation microprocessor 13 fetches offset information stored in EEPROM 15. It then uses this information to compute gas flow rate and constituent concentration.

Microprocessor 13 computes the concentration of a gas constituent according to the formula:

$$P = C_1 T + C_2 O_1 + C_3 (t_{FB})$$

Microprocessor 13 computes the standard gas flow rate according to the formula:

$$Q = ABS(C_4(t_F - t_B)) + C_5 O_2$$

wherein P is the percentage concentration of measured gas constituent, $C_1$, $C_2$, $C_3$, $C_4$, $C_5$ are constants for the ultrasonic assembly 23, T is the temperature of the gas, $t_{FB}$ is the time of travel back and forth through the sensor chamber 24, $t_F$ is the time of travel in the forward direction between sensors 4 and 5, $t_B$ is the time of travel in reverse direction between sensors 5 and 4, $O_1$, $O_2$ are offset values determined at calibration.

Figure 6:
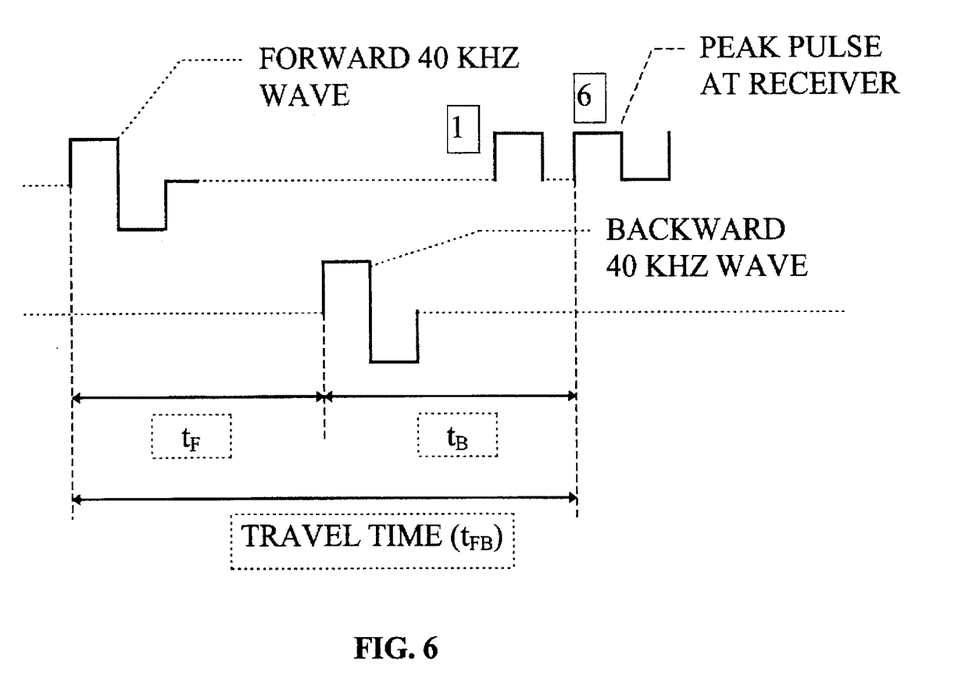
FIG. 6 is a diagrammatic view of transmit/receive pulses.
Figure 7:
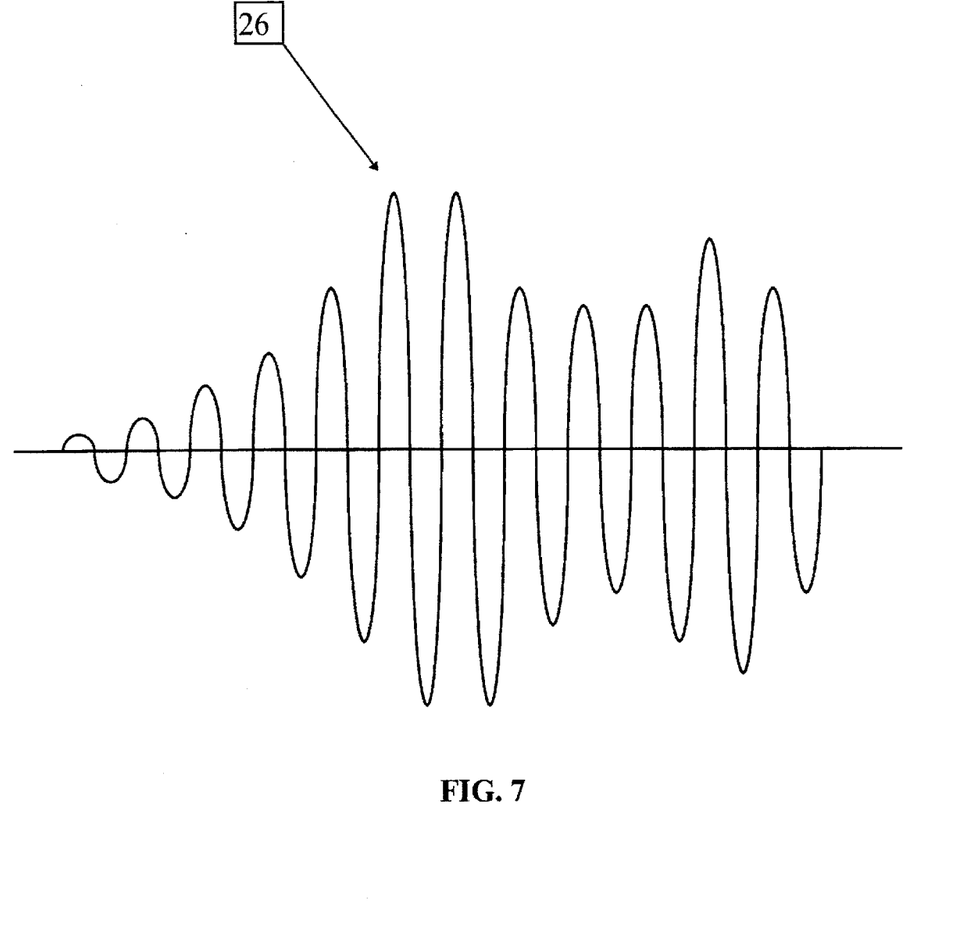
FIG. 7 is a diagrammatic view of a receiver piezoelectric transducer resonating to its peak amplitude in response to a single ultrasonic wave.

In referring to FIG. 6 the transmit/receive waves are accurately disclosed. As soon as the back traveling wave reaches receiver, receiving piezoelectric transducer begins to resonate at its resonant frequency. The amplitude of oscillations grows rapidly and approximately at 6th pulse 26 reaches its peak. As the phase of the peak pulse can be most accurately detected, the peak pulse 26 is the most accurate point of reference. Thus all times ($t_F$, $t_B$, $t_{FB}$) are measured from the time of transmission to the time of peak pulse at the receiver.

It will be appreciated that various modifications and changes may be made to the above described preferred embodiment of a gas concentration and/or flow sensor without departing from the spirit and scope of the following claims. Although the sensor has been described for measuring both the standard flow rate of a gas and the concentration of a component of the gas, it will be appreciated that the sensor may be used for measuring only one of these properties when there is no need to measure the other property.

Having thus described the invention, I claim:

1. A method of measuring the ratio of gasses in a binary gas mixture comprising the steps of;

transmitting a first sound wave from an initial transmission point through the gas mixture, detecting the arrival of said first sound wave at a receiving point a preselected distance from said initial transmission point, then, after a given delay, transmitting an echo wave from said receiving point in the opposite direction, through the gas mixture, back to said initial transmission point, said echo wave being of the same frequency and wave length as said first sound wave and superimposed thereon, receiving said echo wave at said initial transmission point, then measuring the travel time from the initial transmission to the time of reception of said echo wave to provide a measure of the relative proportions of the gases in said mixture, and providing a display indicative of the relative proportions of said gasses.

2. The method of claim 1 further including the steps of;

computing the relative proportions of the gasses in said mixture with a microprocessor apparatus, controlling transmission of said first sound wave and said echo wave by said microprocessor apparatus, said microprocessor apparatus having an internal clock with a frequency of at least 125 times greater than the frequency of said first sound wave.

3. The method of claim 2 wherein said delay is constant and is within 2% or less of the wave length of said first sound wave, said method further including the step of;

offsetting said delay by an offset value stored in an EEPROM connected with said microprocessor apparatus.

4. The method of claim 3 wherein said first sound wave and said echo wave each comprise a single wave composed of a single positive and a single negative cycle.

5. The method of claim 1 wherein said binary gas mixture flows in a given direction and further including the steps of;

measuring the travel time of said first sound wave from transmission to detection and return travel time of said echo wave to said initial transmission point, and calculating the difference between the travel times of said waves to determine the gas flow rate.

6. The method of claim 4 including the step of;

utilizing the peak amplitude of the echo wave at the initial transmission point to measure the total wave travel time.

7. The method of claim 6 including the step of;

measuring the gas temperature of said gas mixture between said initial transmission point and said receiving point during wave transmission, and inputting said microprocessor apparatus with gas temperature data for computing the relative proportion of the gasses in said mixture.

8. The method of claim 4 wherein said predetermined distance between said initial transmission point ad said receiving point is greater than ten wavelengths of said first sound wave.

9. The method of claim 4 wherein said first sound wave is transmitted at a frequency of 40 KHz.

10. In a sensor for determining the composition of a binary gas mixture, said sensor including a sealed gas chamber for containing said gas mixture, first and second acoustic transducers mounted a predetermined distance apart in said chamber and means for selectively energizing said transducers to transmit acoustic waves through said gas mixture, a gas ratio measurement system comprising in combination;

a switching network for alternately conditioning said transducers for transmitting and receiving said sound waves, and a microprocessor apparatus connected to said switching network for conditioning said transducers such that one said transducers is energized to transmit a first sound wave of a given frequency and wave length to be received by the other transducer and then, immediately upon detection of said first sound wave, converting said other transducer to a transmitter and, within a given constant delay time, send a return echo sound wave of the same frequency and wave length to said one transducer superimposed on said first sound wave, whereby the time from initial transmission of said first sound wave to the time of reception of said echo sound wave may be utilized to calculate the gas ratio measurement.

11. The sensor of claim 10 wherein;

said microprocessor apparatus has an internal clock frequency of at least 125 times higher than the frequency of said first sound wave, whereby said echo sound wave can be generated within a delay of 2% of the wave length of said first sound wave, and an EEPROM connected to said microprocessor with means to apply an offset value to offset said delay.

12. In a sensor for determining the composition of a binary gas mixture, said sensor including a sealed gas chamber for containing said gas mixture, said chamber comprising a hollow conduit having end walls and an elongated cylindrical side wall, first and second acoustic transducers mounted a predetermined distance apart in said chamber and means for selectively energizing said transducers to transmit acoustic waves through said gas mixture, a gas ratio measurement system comprising in combination;

a first gas flow port in said side wall at one end of said conduit and a second gas flow port in said side wall at the other end thereof, means for generating gas flow in a given direction within said conduit between said gas ports, a switching network for alternately conditioning said transducers for transmitting and receiving said sound waves, and a microprocessor apparatus connected to said switching network for conditioning said transducers such that one said transducers is energized to transmit a first sound wave of a given frequency and wave length to be received by the other transducer and then, immediately upon detection of said first sound wave, converting said other transducer to a transmitter and, within a given constant delay time, send a return echo sound wave of the same frequency and wave length to said one transducer superimposed on said first sound wave, whereby the time from initial transmission of said first sound wave to the time of reception of said echo sound wave may be utilized to calculate the gas ratio measurement, said microprocessor apparatus including means to measure the difference between the travel time of said first sound wave and said echo sound wave and to calculate the flow rate of said gas therefrom.

13. The sensor of claim 10 wherein said first sound wave and said echo sound wave comprise single sound waves composed of a single positive and a single negative cycle.

14. The sensor of claim 10 wherein;

said microprocessor includes means for utilizing the peak amplitude pulse at the reception of said echo sound wave to determine the end of wave travel time.

15. The sensor of claim 10 wherein;

the predetermined distance between said first and second transducers is greater than ten wavelengths of said first sound wave.

16. The sensor of claim 10 including;

a temperature sensor mounted in said chamber substantially halfway between said first and second transducer, and means connecting said temperature sensor to said microprocessor apparatus for supplying temperature data thereto during wave travel of said first and echo sound waves.

17. The sensor of claim 12 including;

a temperature sensor mounted in said chamber substantially halfway between said first and second transducers and means connecting said temperature sensor to said microprocessor apparatus for supplying temperature data thereto during wave travel of said first and echo sound waves, said transducers, said gas flow ports and said temperature sensor being sealed to said chamber by means of non out-gassing epoxy adhesive.

18. The sensor of claim 10 wherein;

said chamber comprises a hollow cylinder, the inner diameter of the chamber being less than two but more than one wavelengths of said first sound wave.

19. The sensor of claim 18, wherein said hollow cylinder is approximately 11 centimeters in length.

20. The sensor of claim 12 wherein;

said microprocessor apparatus has an internal clock frequency of at least 125 times higher than the frequency of said first sound wave, whereby said echo sound wave can be generated within a delay of 2% of the wave length of said first sound wave, and an EEPROM connected to said microprocessor with means to apply an offset value to offset said delay.

21. The sensor of claim 12 wherein said first sound wave and said echo sound wave comprise single sound waves composed of a single positive and a single negative cycle.

22. The sensor of claim 12 wherein;

said microprocessor includes means for utilizing the peak amplitude pulse at the reception of said echo sound wave to determine the end of wave travel time.

23. The sensor of claim 12 wherein;

the predetermined distance between said first and second transducers is greater than ten wavelengths of said first sound wave.

24. The sensor of claim 12 wherein;

said chamber comprises a hollow cylinder, the inner diameter of the chamber being less than two but more than one wavelengths of said first sound wave.

25. The sensor of claim 12 wherein said hollow cylinder is approximately 11 centimeters in length.

* * * * *